(12) United States Patent
Milgrom

(10) Patent No.: US 12,397,168 B2
(45) Date of Patent: Aug. 26, 2025

(54) LIGHT THERAPY BED WITH ILLUMINATED MESH SUPPORT STRUCTURE

(71) Applicant: Power Medicine, LLC, Santa Ana, CA (US)

(72) Inventor: Asher Milgrom, Irvine, CA (US)

(73) Assignee: Power Medicine, LLC, Santa Ana, CA (US)

( * ) Notice: Subject to any disclaimer, the term of this patent is extended or adjusted under 35 U.S.C. 154(b) by 0 days.

(21) Appl. No.: 18/990,988

(22) Filed: Dec. 20, 2024

(65) Prior Publication Data

US 2025/0205509 A1 Jun. 26, 2025

Related U.S. Application Data

(60) Provisional application No. 63/613,810, filed on Dec. 22, 2023.

(51) Int. Cl.
*A61N 5/00* (2006.01)
*A61N 5/06* (2006.01)
*A61B 17/00* (2006.01)

(52) U.S. Cl.
CPC ........ *A61N 5/06* (2013.01); *A61B 2017/0019* (2013.01); *A61N 2005/007* (2013.01); *A61N 2005/0626* (2013.01); *A61N 2005/0638* (2013.01); *A61N 2005/0639* (2013.01); *A61N 2005/0652* (2013.01); *A61N 2005/0659* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 4,234,907 A | 11/1980 | Daniel | |
| 6,063,108 A | 5/2000 | Salansky | |
| 6,443,978 B1 * | 9/2002 | Zharov | A61N 5/0616 606/2 |
| 7,147,653 B2 | 12/2006 | Williams et al. | |

(Continued)

FOREIGN PATENT DOCUMENTS

CN 115212468 A 10/2023

*Primary Examiner* — Sana Sahand
(74) *Attorney, Agent, or Firm* — Hall Estill Law Firm

(57) ABSTRACT

Apparatus and method for applying photobiomodulation (PBM) light illumination therapy to a patient. A light therapy bed has a PBM mesh structure supported by a rigid frame to form a patient support surface adapted to contactingly support the patient. The mesh structure has respective illuminating and non-illuminating strands which interconnect to form a conformable, open hammock-type support structure with an array of mesh apertures extending therethrough. The illuminating strands have light sources such as light emitting diodes (LEDs) which emit electromagnetic radiation at one or more selected frequencies. A control circuit activates the light sources in accordance with a selected modulation profile. In further embodiments, an upper PBM mesh structure can be lowered to concurrently irradiate the patient. The open mesh areas can constitute 50% or more of the overall areal extent of the mesh to provide patient cooling and application of additional light from a supplemental source.

25 Claims, 9 Drawing Sheets

(56) References Cited

U.S. PATENT DOCUMENTS

| | | | |
|---|---|---|---|
| 8,870,740 B2 | 10/2014 | Clegg et al. | |
| 9,126,034 B1 | 9/2015 | Deroberts | |
| 9,604,072 B2 | 3/2017 | Brezinski | |
| 10,363,434 B2 | 7/2019 | Marchese et al. | |
| 11,020,611 B1* | 6/2021 | Falk | A61N 5/0621 |
| 11,103,724 B2 | 8/2021 | Powell | |
| 11,285,335 B2 | 3/2022 | Asprey et al. | |
| 11,497,930 B2 | 11/2022 | Powell | |
| 11,547,869 B2 | 1/2023 | Dijkstra | |
| 2002/0120312 A1* | 8/2002 | Butler | A61N 5/0616 607/90 |
| 2004/0231056 A1 | 11/2004 | Jansen | |
| 2006/0217787 A1* | 9/2006 | Olson | A61N 5/0616 607/88 |
| 2012/0035690 A1 | 2/2012 | Turtzo | |
| 2013/0253621 A1* | 9/2013 | DeLuca | A61N 5/0618 607/94 |
| 2016/0154170 A1 | 6/2016 | Thompson et al. | |
| 2019/0126057 A1* | 5/2019 | Feldreich | A61N 5/0616 |
| 2022/0288349 A1* | 9/2022 | Falk | A61G 11/00 |

\* cited by examiner

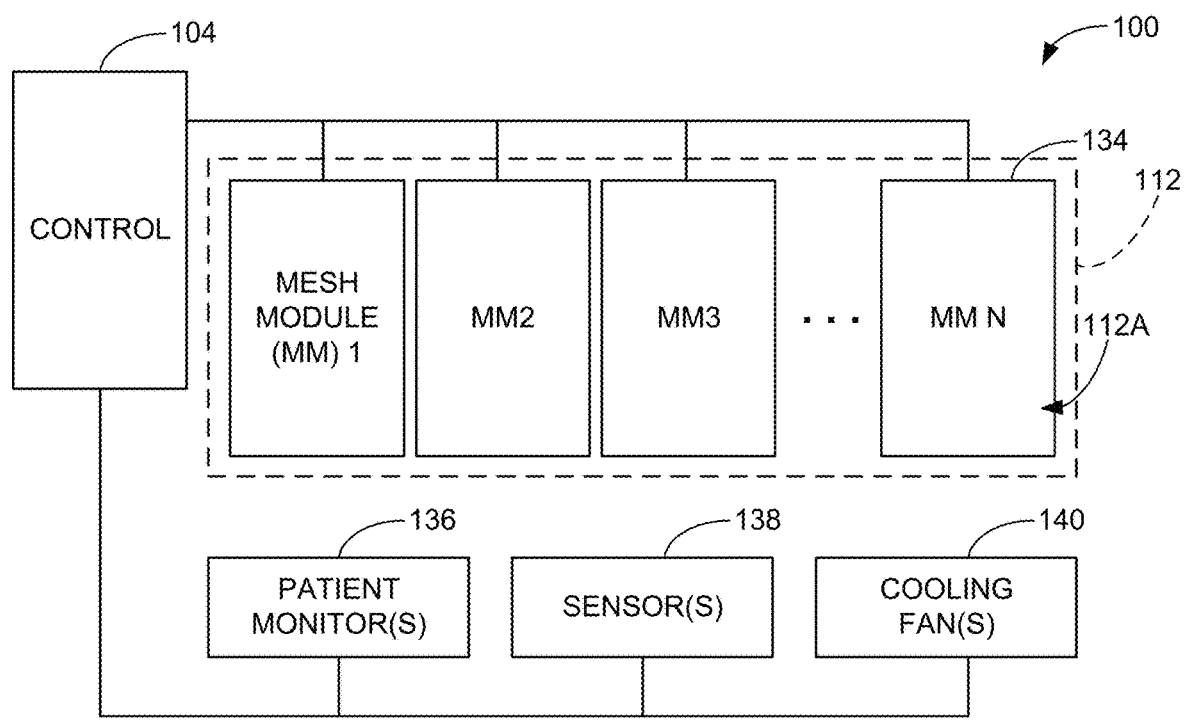
FIG. 3
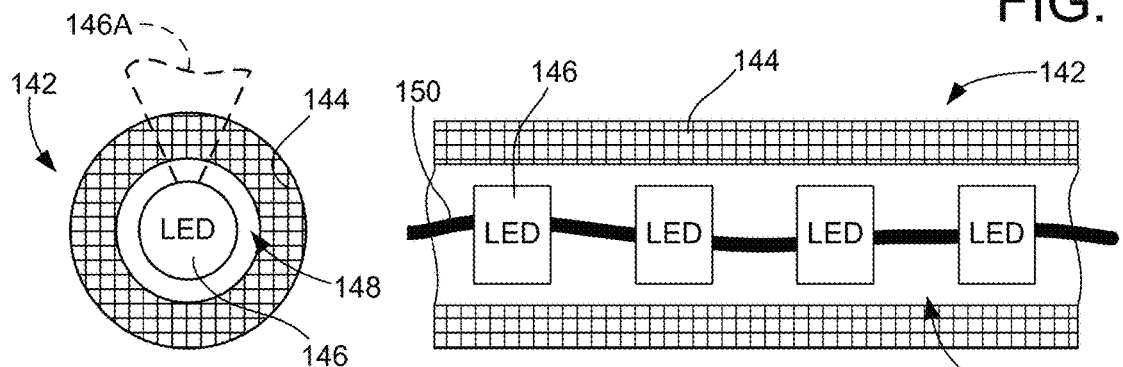
FIG. 4A
FIG. 4B
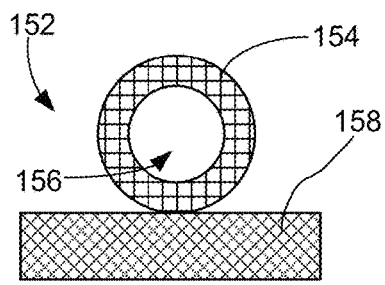
FIG. 4C
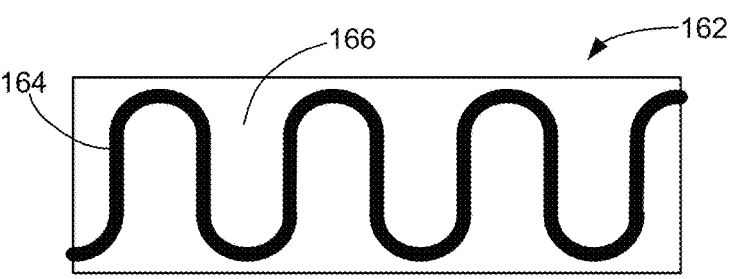
FIG. 4D

LIGHT THERAPY BED WITH ILLUMINATED MESH SUPPORT STRUCTURE

RELATED APPLICATION

The present application makes a claim of domestic priority under 35 U.S.C. 119(e) to U.S. Provisional Patent Application No. 63/613,810 filed Dec. 22, 2023, the contents of which are hereby incorporated by reference.

BACKGROUND

The benefits of light therapy are well known, if not fully understood or appreciated by all members of the medical community. Light therapy generally involves irradiating a patient with controlled amounts of electromagnetic radiation, such as from light emitting diodes (LEDs) or other light sources, in the visible or near visible spectrum. The applied light can be single or multi-spectral with various wavelengths, pulse rates, pulse shapes and intensities.

It has been established that light therapy can provide numerous beneficial effects upon many human biological/physiological systems (e.g., immunological, neurological, dermatological, etc.). Specific frequencies of light energy are particularly important for their effect on mitochondria and the efficient production of ATP (adenosine triphosphate), which is the essential fuel of cellular life and all physiological activity.

Light therapy technology is sometimes referred to as photobiomodulation (PBM) and has a wide spectrum of market applications. As PBM has proven effective in the treatment of many diseases, it is expected to gain rapid expansion throughout the medical industry, allowing medical providers to customize treatment protocols for individual patients in their offices, as well as placing PBM apparatus in the homes of patients who need daily treatments. Furthermore, the same PBM apparatus used by doctors can be programed to be safely utilized by people who are not medically trained, to provide relief from stress, to improve sleep, to increase overall energy, to enhance beautiful skin, and overall to enhance the health and vitality of any user. Therefore, industries such as health clubs, athletic and fitness centers and the homes of private individuals are also viable clients of PBM technology.

A number of light bed devices have been proposed in the art to provide light therapy to a patient. The devices can take a variety of forms, but many take a construction similar to that of a conventional tanning bed. In such devices, a patient lays on a transparent base surface, such as a layer of acrylic or plexy glass, and an underlying array of light sources (e.g., fluorescent, LED, etc.) shine through the base surface to irradiate the back side of the patient. As desired, a similar arrangement can be provided in a retractable cover to provide concurrent irradiation of the front side of the patient.

A clam shell type arrangement is commonly employed so that the patient lays down on the base surface and the upper surface is lowered to enclose the patient in an essentially closed housing. Other light bed configurations take a more open configuration, such as through the use of a horizontal lighting panel that is arranged above and extends over the patient to project the light downwardly onto the front of the patient.

While operable, these and other existing designs provide a number of disadvantages relating to the comfort of the patient and the effectiveness of the light treatment. For example, if a clear hard surface is used to support the patient, the surface will not uniquely conform to the contours of the patient's body. This is true even if the surface is curvilinearly shaped. It is conventionally (though erroneously) thought that use of a non-conformable, hard surface is required because the hard surface is translucent or transparent and serves as a medium to allow the passage of the administered light therethrough. In such systems, it may be important to maintain the shape of the underlying surface so as to not interfere or alter the properties of the transmitted light.

A related problem is that the patient must normally disrobe, at least to an extent, in order for the administered light to directly shine upon the skin of the patient and penetrate through the skin into the interior portions of their body. If an enclosed structure is used, such as a clamshell housing, the patient will likely perspire or otherwise become excessively heated. While some forms of light therapy may benefit from administration at an elevated core body temperature, it is nonetheless difficult to regulate the temperature within an enclosed structure.

The accumulation of perspiration on the skin of the patient can interfere with the transmission of light as intended. Also, a sweat soaked device increases concerns of transferring contaminants from patient to patient, and thus will require careful and thorough cleaning and disinfection between each successive patient.

Finally, as a rule, many patients find it unpleasant to lay on a hard or flexible plastic surface for a period of time, since exposed skin tends to adhere to the surface during and after the treatment session.

Accordingly, there remains a continual need for improvements to address these and other limitations associated with the existing art. It is to these and other improvements that various embodiments of the present disclosure are generally directed.

SUMMARY

Various embodiments of the present disclosure are generally directed to systems and methods for applying photobiomodulation (PBM) light illumination therapy to a human patient.

Without limitation, some embodiments provide a light therapy bed with a PBM mesh structure supported by a rigid frame to form a patient support surface adapted to contactingly support the patient. The mesh structure has respective illuminating and non-illuminating strands which interconnect to form a conformable, open hammock-type support structure with an array of mesh apertures extending therethrough.

The illuminating strands have light sources such as light emitting diodes (LEDs) which emit electromagnetic radiation at one or more selected frequencies. A control circuit activates the light sources in accordance with a selected modulation profile.

In further embodiments, an upper PBM mesh structure can be lowered to concurrently irradiate the patient. The open mesh areas can constitute 50% or more of the overall areal extent of the mesh to provide patient cooling and application of additional light from a supplemental source.

These and other features and advantages of various embodiments can be understood from a review of the following detailed description in conjunction with the accompanying drawings.

BRIEF DESCRIPTION OF DRAWINGS

FIG. 3 is a functional block representation of aspects of the PBM system of FIGS. 1-2 in accordance with some embodiments.

FIGS. 4A through 4D show various alternative constructions for an illuminating mesh structure of the system in different embodiments.

DETAILED DESCRIPTION

Figure 1:
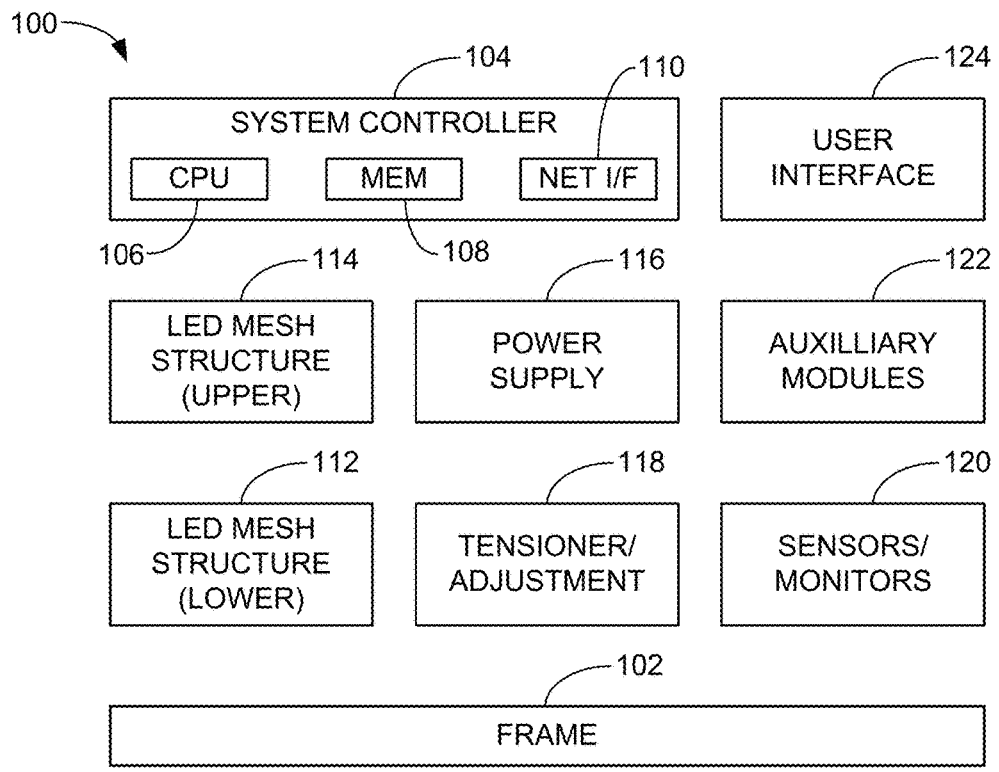
FIG. 1 is a functional block diagram of a PBM light therapy bed system constructed and operated in accordance with various embodiments of the present disclosure.

Various embodiments of the present disclosure are generally directed to an apparatus and method for administering PBM light therapy to a patient.

As explained below, some embodiments utilize a conformable, open light therapy bed arrangement. Generally, the bed can take the form of a hammock-type bed with an illuminating mesh arrangement of flexible strands (cords) having integrated light sources extending therein. The design conforms to the individual shape of each patient, ensuring their comfort.

While LED lights are one form of particularly suitable light source, such is not necessarily required. Any number of different forms of light sources can be utilized. In some embodiments, the LEDs are arranged much like a flexible "LED rope" or "LED light string," albeit with the features disclosed herein to accommodate the use of such in the intended manner.

The support structure on which the patient reclines is thus a conformable mesh structure having interlocking, illuminating strands (cords) that are woven or otherwise interconnected to provide a soft, comfortable and open support. The strands may be formed of a suitable, durable and clear flexible plastic or similar medical grade material in the form of a tube through which a sequence of adjacent LED lights extend. In this way, the lights are immediately adjacent the skin of the patient, separated only by the thickness of the tube material and the through air gaps extending between adjacent strands.

Substantially any mesh pattern can be used. The illuminated strands can extend longitudinally (e.g., in a direction along the length of the patient) laterally (e.g., in an orthogonal direction across the width of the patient), or in any other desired orientation(s) including multiple directions such as in a criss-cross pattern. Non-illuminating strands (support members) can be woven or otherwise incorporated into the mesh structure to enhance the strength and comfort of the mesh. In one nonlimiting example, the illuminated strands extend laterally and are separated and secured by non-illuminating strands that extend longitudinally. In this arrangement, illuminated "bars" of light extend across the width of the patient. Other arrangements can be used.

A significant amount of open space is provided between adjacent pairs of the strands, as in the case of a conventional net or hammock. The size of these air gap openings, also sometimes referred to as mesh apertures, can vary as required. In some embodiments, the mesh apertures can be as small as about 1-2 inches or less across to upwards of about 7-8 inches or more across. Other sizes for the mesh apertures can be used, including sizes that are larger or smaller than the above ranges. The overall open area in the mesh (e.g., the sum of all of the mesh apertures) may account for 50% or more of the overall areal extent of the bed surface. Other open areal extents can be used, such as from as low as about 20% to upwards of about 90%.

The mesh will be arranged with sufficient density and strength to enable the patient to comfortably move onto, off of, and lay upon the mesh, much like an otherwise conventional hammock type structure. The mesh apertures are sufficiently sized to allow significant amounts of airflow to flow through the mesh structure directly onto the patient's skin, to cool the patient, thereby reducing to the point of eliminating perspiration. The volume and intensity of the airflow can be made adjustable enabling maximum comfort to each individual patient.

Further embodiments provide a corresponding upper mesh structure that is suspended immediately above the patient to irradiate the front side of the patient. As with the lower mesh structure described above, the upper mesh structure may be formed of illuminated strands woven or otherwise arranged into an interlocking pattern. This upper pattern may be the same as, or different from, the lower pattern.

While some embodiments contemplate that the upper mesh structure may be lowered into a position near the patient, because of the low weight and flexibility of the mesh, the mesh may be further lowered so as to contact and lay across the top surface of the patient in direct engagement with the patient's body. A suitable frame can be provided to both support the lower mesh and, as needed, adjustably raise and lower the upper mesh to a suitable position. Because of the open nature of the upper and lower mesh structures, patient discomfort due to claustrophobia or overheating is avoided.

The overall extents of the upper and lower mesh structures can vary, but as with conventional LED type beds, a standard size may be provided of sufficient dimensions to accommodate a normal human adult. Some embodiments provide an overall size of about 84 inches (7 feet) in length by about 48 inches (4 feet) in width to accommodate patients of different heights and sizes. Other sizes can be used. The frame may also have the capability of being raised or lowered to facilitate patients getting into and out of the bed structure. Tensioning and attachment mechanisms are also utilized as required.

The respective mesh structures can be uniform and each integrated into a single overall length and width, or can be modular. Some modular arrangements may provide different sections with different types of LEDs that can be plugged into the system. For example, a number of modules, such as three (3) to eight (8) modules, can be used to provide different types of light therapy to different portions of the patient's body (e.g., one section for the head/shoulder area, another for the upper leg area, etc.).

This modular approach further allows light to be tailored to specific regions of the body, so that it is not necessarily required that the entire body of the patient be illuminated. Hook and loop (Velcro® brand) fasteners and plug in connectors can be used to allow sections of the bed to be installed and removed as required. Furthermore, for each individual patient, given their specific physiological needs, the apparatus can easily and quickly be customized with specific frequencies of light that provide the maximal therapeutic benefits tailored to their unique needs.

A control system provides power for the bed, including the application of electrical power to the various LEDs with characteristics selectable by the therapy administrator. Different voltages, currents, power levels, waveforms, timing durations and pulse widths can be utilized. The control system may include one or more power supplies to provide electrical power for the system, as well as regulation circuitry, sensors, appliances, cooling fans, heating elements, patient monitoring equipment, and so on.

It is contemplated that the control system will be operated under the control of a system controller which may incorporate one or more programmable processors and associated programming to carry out various functions. A user interface can also be provided, as well as network connections including to a remote server, etc.

In some embodiments, an array of lights with different characteristics (such as different wavelengths, constructions, etc.) are provided within the mesh structure. A switching circuit can be used to switch in particular lights within the array, while leaving others of the lights in a deactivated state, to provide a desired spectral illumination profile.

The mesh structure is provided with sufficient strength to bear the weight of the patient without placing undue stress upon the illuminating strands. In some embodiments, weight bearing (support) strands within the mesh are separated from the strands that supply the light. In these arrangements, only the support strands can be provided with an adjustable tension capability, while the strands that supply the light will bear essentially no weight of the patient. In these and other embodiments, the illuminated strands may be placed slightly lower in elevation to the support strands (e.g., such as by a distance of a few millimeters, etc.), or otherwise arranged such that little or no stress is applied to the illuminated strands.

The control aspects of the system enable a first patient to be subjected to a first treatment profile using a first set of applied parameters (including a first set of wavelengths of applied light), and the same mesh structure can be used to subsequently provide a different, second treatment profile to a second patient using a different, second set of applied parameters (including a second set of wavelengths of applied light). This arrangement allows the same mesh structure to be selectively activated to provide each of the different first and second treatment profiles (as well as other treatment profiles to other patients as needed).

Any color lights can be used as desired (e.g., red, orange, blue, green, yellow, etc.) over substantially any desired wavelength spectral range. In some embodiments, wavelengths are provided of from around 500 nanometers, nm (10-12 meters) up to around 1500 nm. Other wavelengths can be used, including wavelengths greater or less than this range.

There are several primary factors that provide a particular therapeutic light application profile: (1) power, (2) frequency, (3) modulation, and (4) distance. Power generally relates to the intensity of the emitted light, such as on the basis of absolute power and/or average power (in watts, etc. per area of skin irradiated). Frequency generally relates to the color/wavelength of the emitted light, including multiple wavelengths being concurrently or sequentially applied.

Modulation generally relates to various factors associated with the applied light, including timing, pulse intervals, pulse waveforms, rest periods between active periods, and so on. Distance relates to the distance from the light to the patient, which is highly selectable and can be set as required for both upper and lower mesh structures. Other factors can be utilized to tailor a particular profile as well. The control features of the various embodiments disclosed herein can accommodate substantially any desired application profile, as explained more fully below.

The open nature of the mesh structure not only promotes patient comfort and conformed application of the applied light, but also enables other treatment protocols to be applied to the patent during or otherwise in conjunction with the light therapy treatment. For example, an intravenous (IV) connection can be made to the patient, allowing the administration of beneficial therapeutic agents, blood ozonation, etc. to be carried out. Blood samples can be taken of the patient before, during and/or after a light therapy treatment session to assess patient status and response. Other related therapies can be carried out as well (e.g., transcranial magnetic stimulation, audio stimulation, oxygen therapy, etc.). Sensory obscuration devices (eye covers, ear phones, etc.) can be worn by the patient as part of the use of the system.

While the various embodiments contemplate a bed as the light therapy structure, other forms of structures can be used. For example, a chair or similar type of support device can be similarly configured so that the patient sits down in a sitting position rather than laying in a prone position as described above. Nonetheless, it is contemplated that at least some portion of the light therapy structure supports, at least in part, the weight of the patient so that at least some of the skin of the patient is brought into supportive contact with and by the illuminated mesh structure.

These and other features and advantages of various embodiments can be understood beginning with a review of FIG. 1, which provides a functional block representation of a PBM light bed therapy system 100. The system 100 includes a number of components including a support frame 102 that provides a rigid support framework for other aspects of the system.

A system controller 104 provides top level control for the system 100. While not limiting, the controller 104 may include one or more programmable processors with associated programming in the form of software and/or firmware stored in a suitable memory for execution. Hardware based processors and other logic circuitry can additionally or alternatively be used.

In FIG. 1, the controller 104 is shown to include a programmable processor in the form of a central processing unit (CPU) 106, memory (MEM) 108, and a network interface (NET I/F) 110. Other arrangements for the controller can be used, including use of a remotely located controller that is at a different location than remaining portions of the system 100, the use of machine learning (ML) systems, etc.

Figure 2:
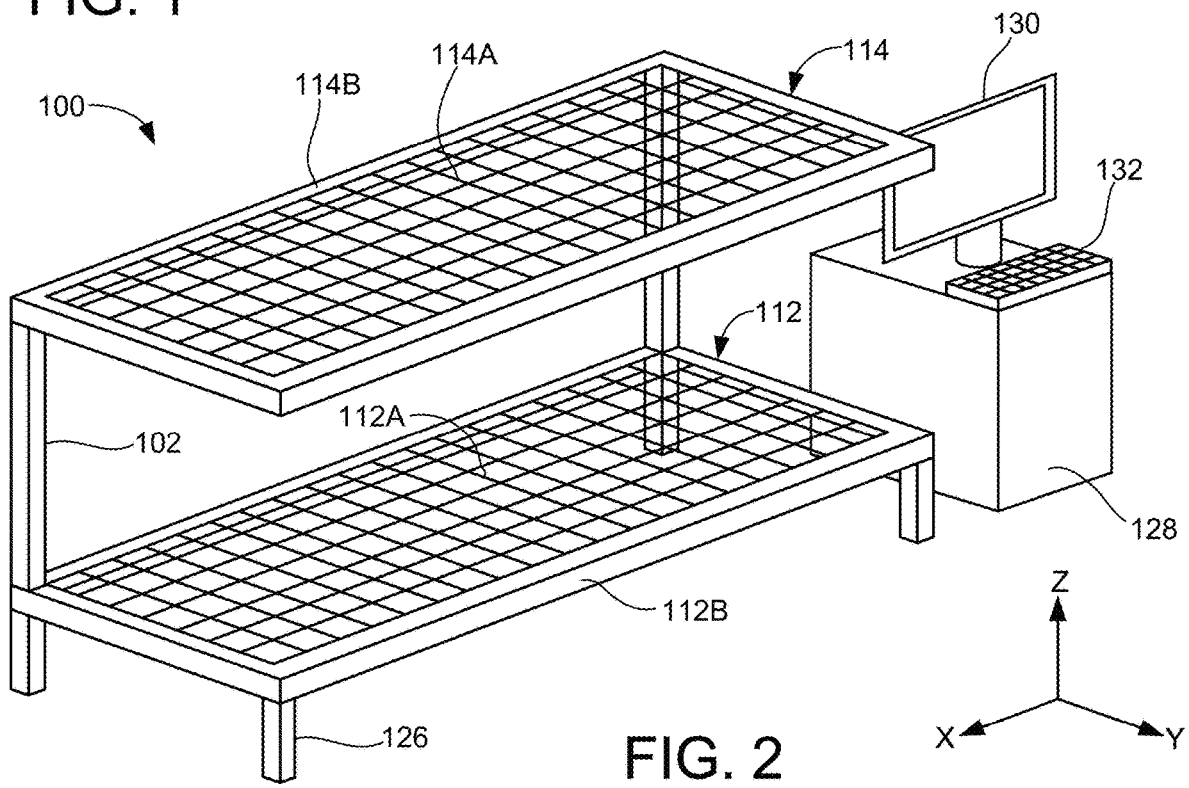
FIG. 2 is a simplified isometric depiction of the PBM system of FIG. 1 in accordance with some embodiments.

The system 100 further includes a lower mesh structure 112 and an upper mesh structure 114. These are generally arranged as shown in FIG. 2. As explained below, the mesh structures 112, 114 are contemplated as utilizing respective arrays of LEDs, although this is merely exemplary and is not limiting.

The system 100 further has a number of components to support the operation of the mesh structures 112, 114 in administering a light therapy (PBM) session to a patient. These additional components can include a power supply 116, tensioner and adjustment mechanisms 118, various sensors and monitors 120, and additional auxiliary modules 122 (e.g., cooling fans, automated actuators, additional light sources, etc.). A user interface (I/F) 124 is coupled to the controller 104 to enable the administrator to control operation of the system 100.

FIG. 2 provides a simplified schematic representation of the system 100 of FIG. 1 in accordance with some embodiments. Other arrangements can be used, so it will be understood that the arrangement shown in FIG. 2 is merely exemplary and is not limiting. The upper and lower mesh structures 112, 114 are generally rectangular in shape and each respectively include a flexible illuminating mesh 112A, 114A and a corresponding rigid rectangular framework 112B, 114B.

During use, the patient will lay upon the lower mesh 112A of the lower mesh structure 112. The upper mesh structure 114 may be maintained in a stationary position, or may be lowered such that the upper mesh 114A is brought into close proximity with the patient.

Other embodiments use a different configuration such as a bed arrangement with the lower mesh 112A only so that the upper mesh 114A is omitted. Another alternative arrangement provides the lower mesh 112A and a different form of overhead illumination source, such as a rigid structure with an array of LEDs or other lights, a single illumination lamp, etc.

In still another embodiment, the upper mesh structure 114 is conformable so that, once the patient is disposed on the lower mesh structure 112, the upper mesh structure can be lowered and shaped, such as in a curved configuration, so as to be closely spaced to the patient's body at a desired distance therefrom.

For example, an adjustment mechanism of the frame 114B can be configured to impart curvature to the upper PBM mesh structure to conform and position the PBM mesh structure to surround the frontside of the patient at a selected uniform distance therefrom. In each of these alternative embodiments, the intervening distances between the patient and the lights in the respective mesh structures 112, 114 can be controllably set to desired, precise distances.

Each of the rectangular mesh structures 112, 114 have a longitudinal dimension along direction (axis) X, which generally corresponds to the height of the patient as the patient lays upon and is supported by the lower mesh 112A. A Y direction (axis) extends laterally across the patient, and a Z direction is a vertical direction (axis) along which the upper mesh 114A may be raised and lowered.

Support legs 126 can be provided at each corner of the frame 102 to support the lower mesh structure 112 at a desired distance above an underlying floor surface. The legs 126 may be adjustable, including through powered mechanisms, to enable the lower mesh structure 112 to be raised or lowered to different elevational heights suitable for entry and exit by the patient. The support legs 126 further support the frameworks 112B, 114B, which in turn circumferentially extend about and contactingly support each of the respective edges of the respective meshes 112A, 114A.

In the simplified embodiment of FIG. 2, a control cabinet 128 is provided to house at least some aspects of the various components shown in FIG. 1. The user interface 124 from FIG. 1 is shown to include a display monitor 130 and a keyboard 132. In practice, substantially any form of user interface can be utilized including but not limited to a smart phone, tablet, mouse, touch screen, etc. Wired or wireless communication paths can be utilized to enable communication among the various constituent elements of the system 100.

FIG. 3 shows a functional block representation of the system 100 of FIGS. 1-2 in accordance with further embodiments. The system controller 104 from FIG. 1 is shown as a control module operatively coupled to a selected mesh structure (in this case, the lower mesh structure 112). The illuminated lower mesh 112A of the lower mesh structure 112 takes a modular configuration in FIG. 3, being made up of N mesh modules 134 where N is a plural number. Any number of mesh modules 134 can be utilized. In some embodiments, the total number of mesh modules may be on the order of from about three (3) to about eight (8) (e.g., N=3 to 8), although other numbers of modules 134 can be used.

While not necessarily required, in the embodiment of FIG. 3 the mesh modules 134 can be removably installed into the lower mesh structure 112. In this case, the mesh modules 134 may have different illumination characteristics such as LEDs that emit different wavelengths of light, mesh strands arranged into different mesh patterns, etc.

It is contemplated that the mesh modules 134 can be quickly and easily installed, removed and replaced as required using quick release features such as hook and loop fasteners, brackets, hooks, etc. In this way, the system 100 can be configured for the specific physiological and therapeutic needs of an individual patient, and different portions of the patient (such as along the X direction) can be irradiated with different light profiles. Removability of the mesh modules 134 provides other capabilities as well such as ease of cleaning, reconfiguration of the system to accommodate a particular patient, replacement of failed modules, etc.

In some embodiments, the use of mesh modules such as 134 allows specifically tailored light therapy to be concurrently applied to different portions of a patient's body; that is, a selected portion of the body may be subjected to a first form of localized light therapy, and the remainder of the body may be subjected to a second form of localized light therapy.

For example, a patient may have a left leg that has been injured or has been subjected to surgery. The bed can be configured such that one or more modules are installed adjacent the patient's left leg that provide a first profile of applied light therapy specially configured to promote healing of the left leg. The rest of the bed can be configured with other modules that provide a different second profile of applied light therapy, such as one that promotes overall well being or other therapeutic benefits. Other localized light therapy can be supplied to address other patient conditions in other areas; for example, light therapies in the groin region can address issues relating to infertility or other related conditions involving the sex organs, etc.

FIG. 3 further shows the controller 104 to be operatively coupled to various elements including one or more patient monitors 136, sensors 138, cooling fans 140, etc. The patient monitors 136 may include body temperature, pulse, respiration, blood oxygen, and other vital sign monitoring capabilities. The sensors 138 may include ambient temperature measurement, light measurement, motion sensing and other capabilities. The cooling fans 140 may be placed in suitable locations, including above and/or below the patient, to allow cooling air to flow through the respective meshes 112A, 114A. Other elements may be incorporated into the system as required.

FIGS. 4A through 4D provide further details regarding the respective mesh structures 112, 114 in accordance with some embodiments. Other arrangements can be used. As noted above, in some embodiments the respective meshes 112A, 114A are formed at least in part by flexible illuminating strands. FIG. 4A provides an end cross-sectional view and FIG. 4B provides a top cross-sectional view of an exemplary strand 142.

The strand 142 has a flexible, optically transmissive outer jacket or sleeve 144 through which an array of LEDs 146 extend. The outer sleeve 144 may be formed of plastic, rubber, silicone, or other elastomeric material and is contemplated as being clear or otherwise transparent to allow passage of light beams such as represented at 146A through the sleeve media. While a focused beam 146A is shown for simplicity of illustration, it will be recognized that the emitted light may fully extend in all directions away from the LED 146. The selected material used for the outer sleeve may further be selected for ease of cleaning and sterilization between sessions. UV range LEDs can be incorporated into the system for antimicrobial effects.

The LEDs 146 may be spaced apart along an interior channel 148 within the outer sleeve 144, as represented in FIG. 4B. The LEDs 146 are shown to be serially interconnected via one or more conductive paths 150. In practice, substantially any type of conduit routing arrangement can be used including arrangements that facilitate the individual selection and activation of lights, the selection of particular groups of lights for activation, the concurrent selection of all of the lights along a given strand, and so on.

The LEDs 146 may be substantially any color, size and/or shape as desired. Any suitable spacing can be provided for the LEDs 146 along the interior channel 148 of the strand 142, including a spacing interval of essentially zero distance (e.g., the LEDs are in close proximity or even touching) to a relatively large distance (e.g., the LEDs are separated by several multiples of the individual sizes of the LEDs). It will be appreciated that a suitable spacing will be selected that meets the various system requirements of strand flexibility, power consumption, illumination power, heat generation, strength, availability of lights with different wavelength output responses, and so on.

The outer sleeve 144 is shown to take an elongated, cylindrical shape so as to have a circular cross-sectional shape. This is not necessarily required; other cross-sectional shapes can be provided including D-shaped, rectangular, polygonal, etc. It is contemplated, albeit not necessarily required, that the sleeve material will have sufficient tensile strength so as to not substantially elongate after repeated use in supporting the weight of the various patients that utilize the system. In one nonlimiting example, the strand 142 has an overall diameter of on the order of from about 0.5 inches (in) to about 1 in or more, with a sleeve layer thickness of up to about 0.5 in. Other sizes can be used.

FIG. 4C shows another exemplary strand 152 that may be used in further embodiments. The strand 152 is similar to the strand 142 in FIGS. 4A-4B and includes an outer jacket or sleeve 154 with an interior channel 156 to accommodate an array of LEDs (not shown in FIG. 4C for clarity). The sleeve 154 is affixed to an optional reinforcement member 158, which may be formed of a tough flexible fabric material such as nylon, canvas, elastomer, etc. The reinforcement member may be woven, braided, or otherwise configured to have a high tensile strength so that the member has a high resistance to stretching (e.g., is substantially non-elastic).

While the sleeve 154 is shown to tangentially contact the planar member 158, the reinforcement member may wrap around a portion of the outer surface of the sleeve 154. Any number of suitable bonding techniques can be used including adhesives, welding, sewing, etc. to secure the reinforcement member 158 to the sleeve 154.

In this way, the loading supplied to the strand 152 while the patient is being supported by the associated mesh is borne by both the sleeve 154 and (when used) the associated reinforcement member 158. The reinforcement member 158 accommodates most, if not all, of the loading and reduces tensile stress upon the interior LEDs and conductive paths. It is contemplated in some embodiments that the reinforcement member 158 will be placed opposite the patient so that at least a portion of the sleeve will be exposed in a direction towards the patient (e.g., the LEDs 146 and sleeve 154 will be positioned between the patient and the reinforcement member 158).

As noted above, it may be advisable in at least some embodiments to separate the strands that support the weight of the patient's body from the strands that supply the light. Thus, in this alternative embodiment, only the support strands will have adjustable tension capability, while the strands that supply the light will bear little if any weight at all.

FIG. 4D shows yet another illuminating strand 162 that may be used in accordance with further embodiments. In FIG. 4D, a flexible strand 164 is routed along an underlying reinforcement member 166 in a generally serpentine fashion. The strand 164 may have a configuration similar to the strand 142 in FIGS. 4A-4B, and the reinforcement member 166 may have a weaved or fabric configuration similar to the reinforcement member 158 in FIG. 4C. Any suitable routing pattern can be used. The configuration of FIG. 4D is particularly suitable for applications where smaller sized LEDs may be desired. As before, the strand 162 is configured to bear the weight of the patient during use.

As noted above, substantially any desired mesh pattern(s) can be used in the respective upper and lower mesh structures 112, 114 (see FIG. 2). In some cases, these mesh patterns can be the same, or can be different. Different mesh patterns can further be incorporated into different locations along the respective meshes 112A, 114A such as through the use of the mesh modules 134 in FIG. 3.

Figure 5A:
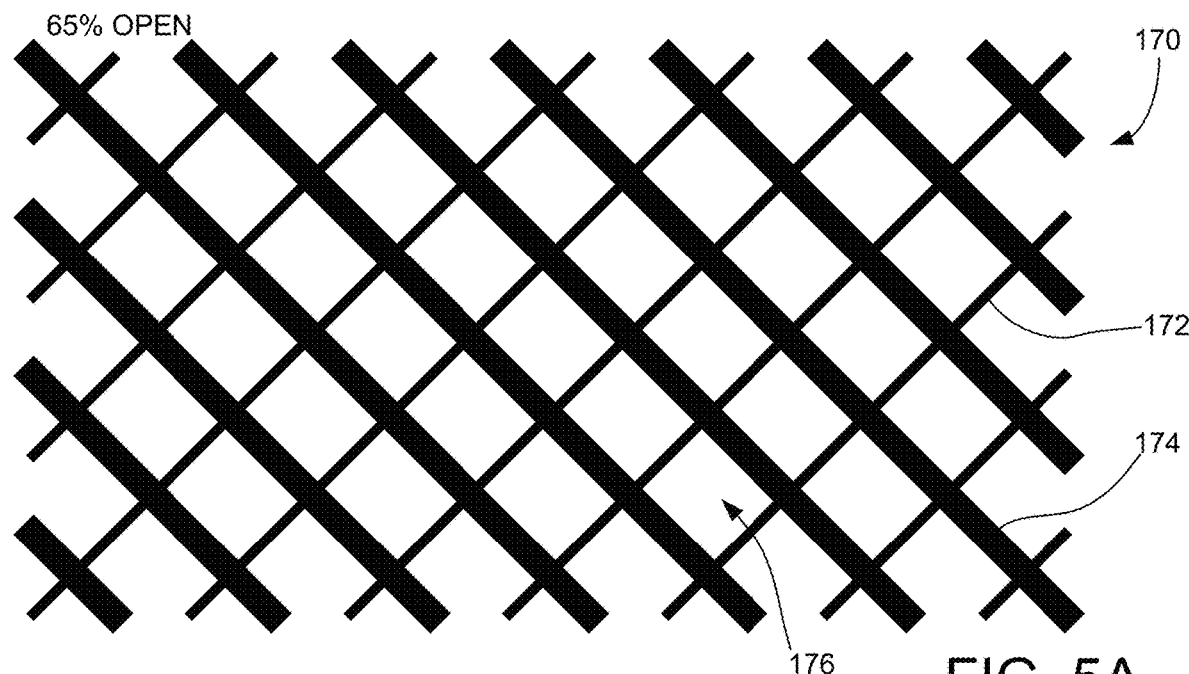
FIGS. 5A and 5B show different mesh patterns that can be utilized in the system in accordance with further embodiments.
Figure 5B:
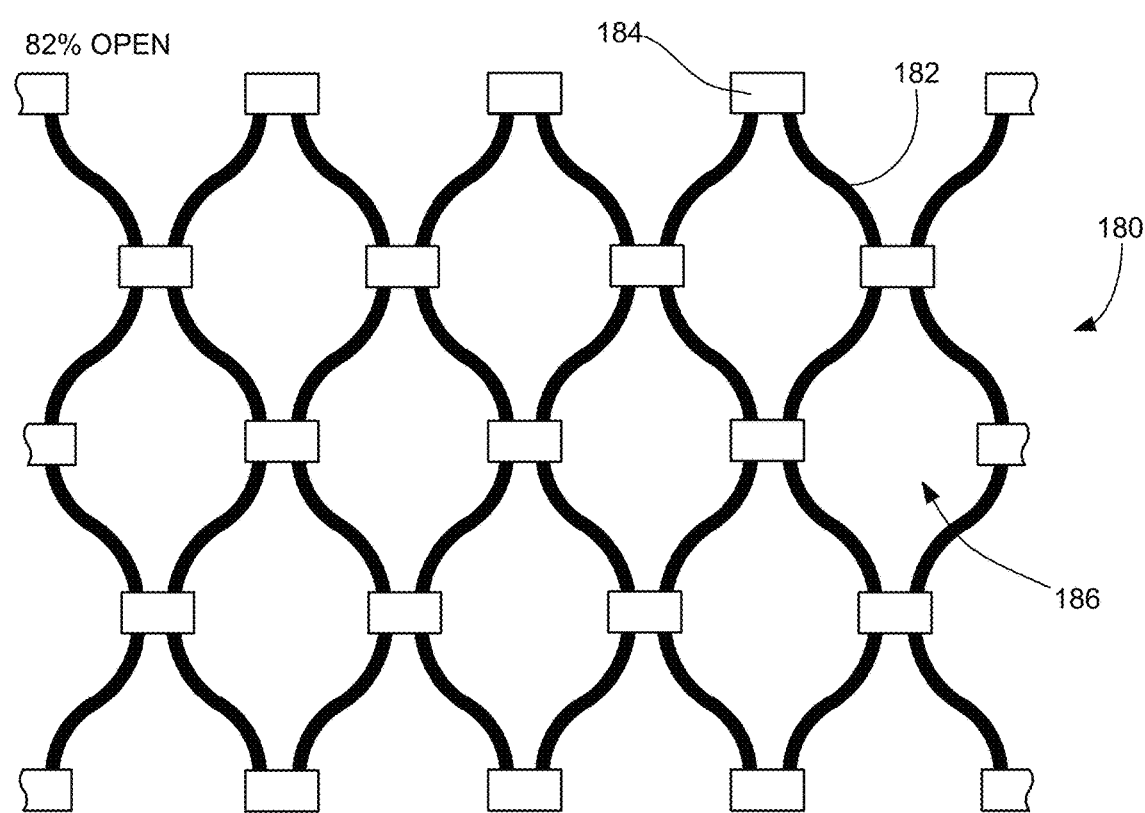

FIGS. 5A and 5B show respective mesh patterns that can be incorporated into either or both of the meshes 112A, 114A. In FIG. 5A, a diamond weave mesh pattern 170 is provided with illuminating strands 172 that interconnect with non-illuminating strands 174. The respective strands 172, 174 diagonally extend with respect to the planar X-Y axes discussed above in FIG. 2. Any suitable angle can be provided with respect to these orthogonal axes, such as nominally 45 degrees. The non-illuminating strands 174 also diagonally extend with respect to the planar X-Y axes at some suitable angle. The non-illuminating strands 174 are wider than the illuminating strands 172, but this is merely for convenience of illustration. In practice, the respective types of strands can take any suitable respective sizes, shapes, angles, and routing paths.

It is contemplated but not necessarily required that the illuminating strands 172 take a construction such as shown by the various embodiments in FIGS. 4A-4D, so that light energy is emitted by the illuminating strands along the lengths thereof. The non-illuminating strands 174, by contrast, do not illuminate the patient but instead are formed of a suitable, high tensile strength material (e.g., nylon straps, etc.). In this way, sufficient strength is provided to the mesh to support the weight of the patient while still providing full irradiation coverage.

Mesh apertures 176 are formed in the open areas between the strands. Each mesh aperture 176 in FIG. 5A takes a generally rectangular (in this case, diamond) shape and is bounded by two immediately adjacent illuminating strands 172 and two immediately adjacent non-illuminating strands 174.

The mesh apertures 176 serve as air flow gaps to permit air flow to pass through the mesh pattern 170 to cool the body of the patient and allow unobstructed transmission of the emitted light from the illuminating strands 172 to the patient.

In some cases, the apertures further allow the application of supplemental light from a secondary light source positioned adjacent the mesh to pass through the mesh and impinge the patient. The secondary light source can take any number of forms including a lamp, an array of lights, another mesh in non-contacting relation to the patient, etc.

While use of supplemental light is not required, the mesh arrangement allows a great deal of flexibility in providing additional light in addition to, or in lieu of, the light from the respective mesh 112A, 114A at different times during a particular application session. The applied light from the mesh may be across one wavelength spectrum and with one application profile, and the applied light from the secondary light source may have a different wavelength spectrum and/or application profile.

Another benefit of the open mesh arrangement as embodied herein is patient access; the open mesh areas provide substantially unfettered access to the patient by attending personnel to attend to patient comfort (e.g., scratching an itch for the patient), administering an IV or other supplemental therapy protocol, etc.

While not limiting, the illuminating strands 172 may pass over and be attached to the top surfaces of the non-illuminating strands 174 in a manner similar to that shown in FIG. 4C (albeit along different cross-wise directions). Different spacings, routing directions, sizes, etc. can be used. In the nonlimiting example of FIG. 5A, the mesh pattern 170 is about 65% open; that is, the mesh apertures 176, in total, account for about 65% of the overall areal extent of the bed surface provided by the pattern. Other open ratios higher or lower than this value can be achieved by varying the number, size and spacing of the respective cross-members 172, 174.

FIG. 5B shows a quilted or net weave pattern 180 formed of illuminating strands 182 interconnected with non-illuminating strands (or members) 184. In this case, the strands are arranged such that the members 184 interconnect different pairs of the strands 182 to enhance strength of the mesh pattern 180. As before, the illuminating strands 182 can be similar to the various configurations shown in FIGS. 4A-4D, or may take some other configuration.

Contoured (quilted) shaped mesh apertures 186 are bounded by each immediately adjacent pair of the illuminating and non-illuminating strands 182, 184. In this case, the pattern 180 is about 82% open. As before, other open ratios can be achieved through adjustments to the pattern.

From FIG. 5B it can be seen that the respective strands (whether illuminating or non-illuminating) can extend fully across the framework opening, or can be localized within the mesh pattern. In a particularly useful alternative arrangement, the order of illuminating and non-illuminating strands in FIG. 5B are reversed; that is, in this alternative embodiment, the strands 184 are illuminating strands (modules) and the strands 182 are non-illuminating, reinforcement strands. The use of the localized modules 184 as illuminating strands enables an operator to selectively install and replace lights into these portions of the mesh as required. The modules 184 can include a plate that receives the LEDs and a clear plastic/silicone cover. Electrical conduits used to supply electrical power to the modules 184 can be routed along the strands 182.

In yet another arrangement, both strands 182, 184 are configured to be selectively illuminating strands, so that treatment can be carried out for a given patient during different times of a selected treatment session using the strands 184, the strands 182, and/or both sets of strands 182 and 184.

The size and shape of the respective mesh apertures 176, 186 will vary depending on a number of factors including the density (e.g., "thread count") of the mesh, the relative widths of the strands, and so on. Nevertheless, it will be understood that the mesh apertures constitute a significant portion of the overall areal extent of the associated mesh pattern. That is, with respect to the overall area bounded by the respective framework (see e.g., 112B, 114B in FIG. 2), a significant portion will be open.

While not limiting, it is contemplated in some embodiments that the accumulated total area of the respective mesh apertures will constitute a majority (e.g., at least 50%) of the overall areal extent of the associated mesh structure. In other embodiments, the accumulated total area of the respective mesh apertures may be 60%, 70%, 75%, 80%, 90%, 95%, more than 95%, or some other percentage of the overall areal extent of the pattern. Other values can be used, including mesh aperture areas less than 50% of the overall areal extent, including as little as 35%, 25%, 20%, or less than 20% of the overall areal extent. Generally, however, a larger open mesh area facilitates greater air flow and light exposure through the mesh.

In at least some cases, a sufficient amount of open mesh area will be selected to provide patient comfort, adequate airflow to reduce perspiration and promote other beneficial effects, reasonable power consumption and heat generation, and light therapy application effectiveness. These factors may vary depending on the needs of each particular patient and/or treatment protocol.

While the various mesh aperture openings in the embodiments disclosed thus far have been shown to be substantially uniform across the entire areal extent of the mesh, other patterns can be provided with mesh apertures of different sizes and shapes at different locations within the mesh pattern. For example, mesh patterns may be provided that have smaller mesh areas in locations adjacent where the patent's body contacts the mesh, at different locations suitable for higher densities of applied light, and so on.

Figure 6:
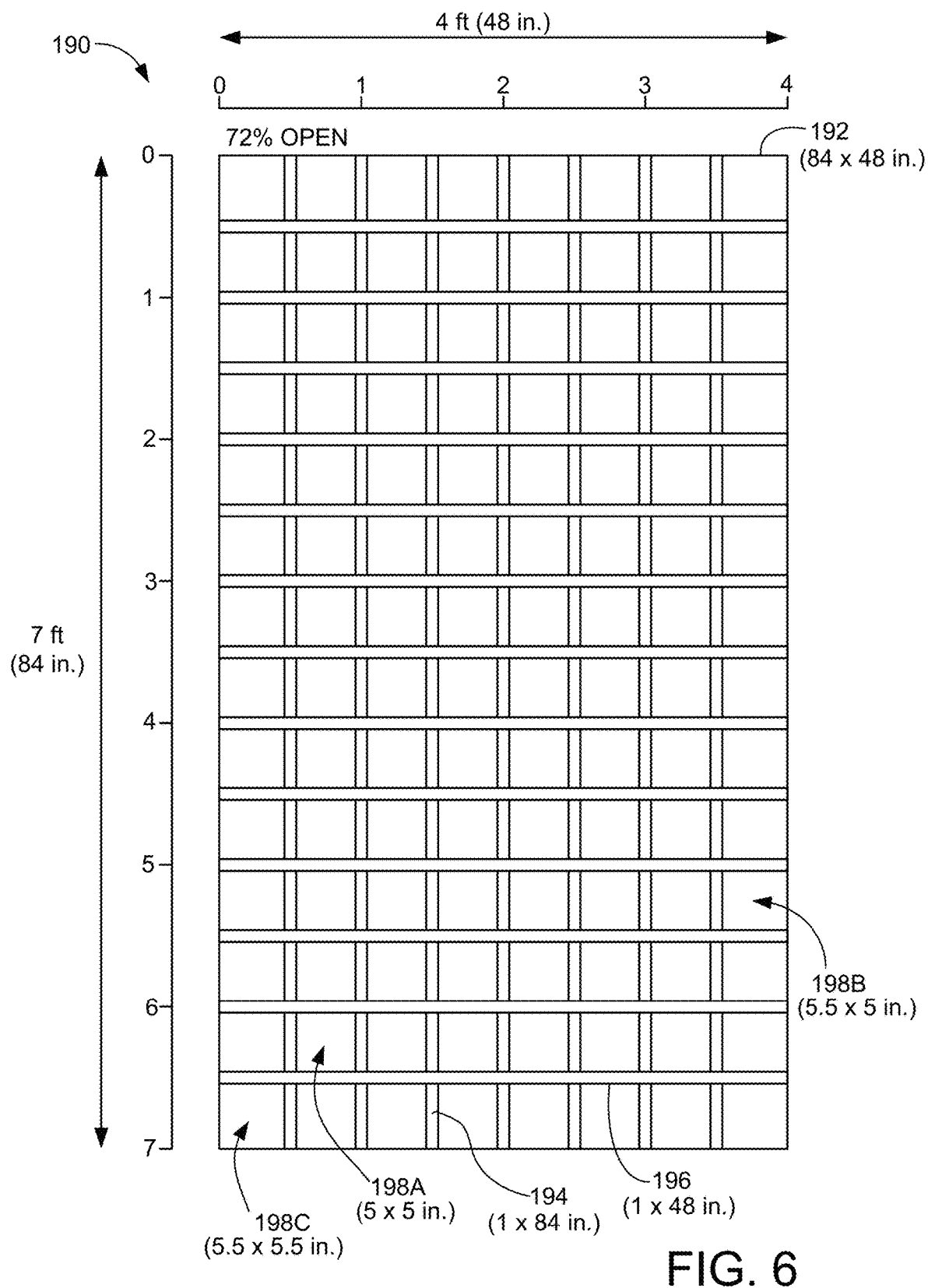
FIG. 6 is a schematic depiction of the relative areal extent of the mesh apertures within another mesh structure in some embodiments.

To give a concrete example, FIG. 6 provides a schematic representation of another mesh structure 190 similar to the mesh structures discussed above. The mesh structure 190 has a rectilinear framework 192 with dimensions of nominally 84 in.×48 in. (e.g., nominally 7 ft×4 ft). Based on this size, the framework 192 provides an overall areal extent of nominally 4032 in.² (84×48=4032).

A series of strands 194, 196 are arrayed across the opening to provide a grid type mesh pattern as shown. Each of the strands 194, 196 is nominally one (1) inch in width. The strands 194 extend longitudinally (e.g., in the X direction) and the strands 196 extend laterally (e.g., in the Y direction). In this example, the strands are nominally arranged on six (6) in. centers, so there are a total of seven (7) longitudinally extending strands 194 and a total of thirteen (13) laterally extending strands 196.

While not limiting, it is contemplated that the longitudinally extending strands 194 are non-illuminating strands and the laterally extending strands 196 are illuminating strands. In this way, the mesh pattern provides laterally extending illumination bars across the width of the mesh (Y-direction). However, in an alternative embodiment, this ordering can be reversed (e.g., the longitudinally extending strands 194 are illuminating and the laterally extending strands 196 are non-illuminating). In yet another alternative embodiment, both sets of strands 194, 196 are configured as illuminating strands.

Mesh apertures are formed in the areas between adjacent sets of these respective strands 194, 196 and between the strands and the framework 192. Based on the simplified example used herein, there will be three different sizes of the mesh apertures within the pattern. The mesh apertures within the medial portion of the mesh 190 are nominally 5 in.×5 in., such as denoted by mesh area 198A. There are a total of sixty (60) such standard-sized mesh areas in FIG. 6.

Mesh areas 198B, which extend along the sides of the framework 192, are each nominally 5 in.×5.5 in. (or 5.5 in.×5 in.) in size. There are a total of thirty-six (36) of these edge mesh areas. Finally, the four (4) corner apertures 198C are each 5.5 in.×5.5 in. in size. This demonstrates that uniformly sized or non-uniformly sized and shaped apertures may be used as required.

The area of the overall areal extent within the framework 192 covered by the strands can be determined by adding up all of the exposed surface area of the respective strands 192, 194, taking into account the fact that the strands periodically overlap. The total areal extent of the longitudinally extending strands 194 is 588 in.² (84*1*7=588). The total areal extent of the laterally extending strands 196 is 624 in.² (48*1*13=624). The amount of overlap of the respective straps is 91 in.² (7*13=91). Hence, the total exposed areal extent of the straps 194, 196 is 1121 in.² (588+624−91=1121). The total mesh aperture area is nominally 2911 in.² (4032−1121=2911).

The total aperture area thus represents approximately 72% (1121/4032=0.72197) of the overall mesh structure areal extent in FIG. 6. Stated another way, the mesh structure 190 is approximately 28% closed (covered) and approximately 72% open. Using narrower strands would tend to increase this ratio, whereas using wider strands would tend to decrease this ratio. Similarly, using closer spacings for respective pairs of immediately adjacent strands would tend to decrease this ratio, whereas using wider spacings would tend to increase this ratio.

Generally, in many cases a larger ratio of open area to overall areal extent will provide enhanced comfort and effectiveness, but the specific amount will depend on the requirements of a given application. It will be appreciated at this point that greater densities (and hence, lower aperture area ratios) may be suitable for some body locations and/or treatment protocols as compared to others. The apertures can be elongated, curvilinear, non-uniform, etc. as required.

Figure 7:
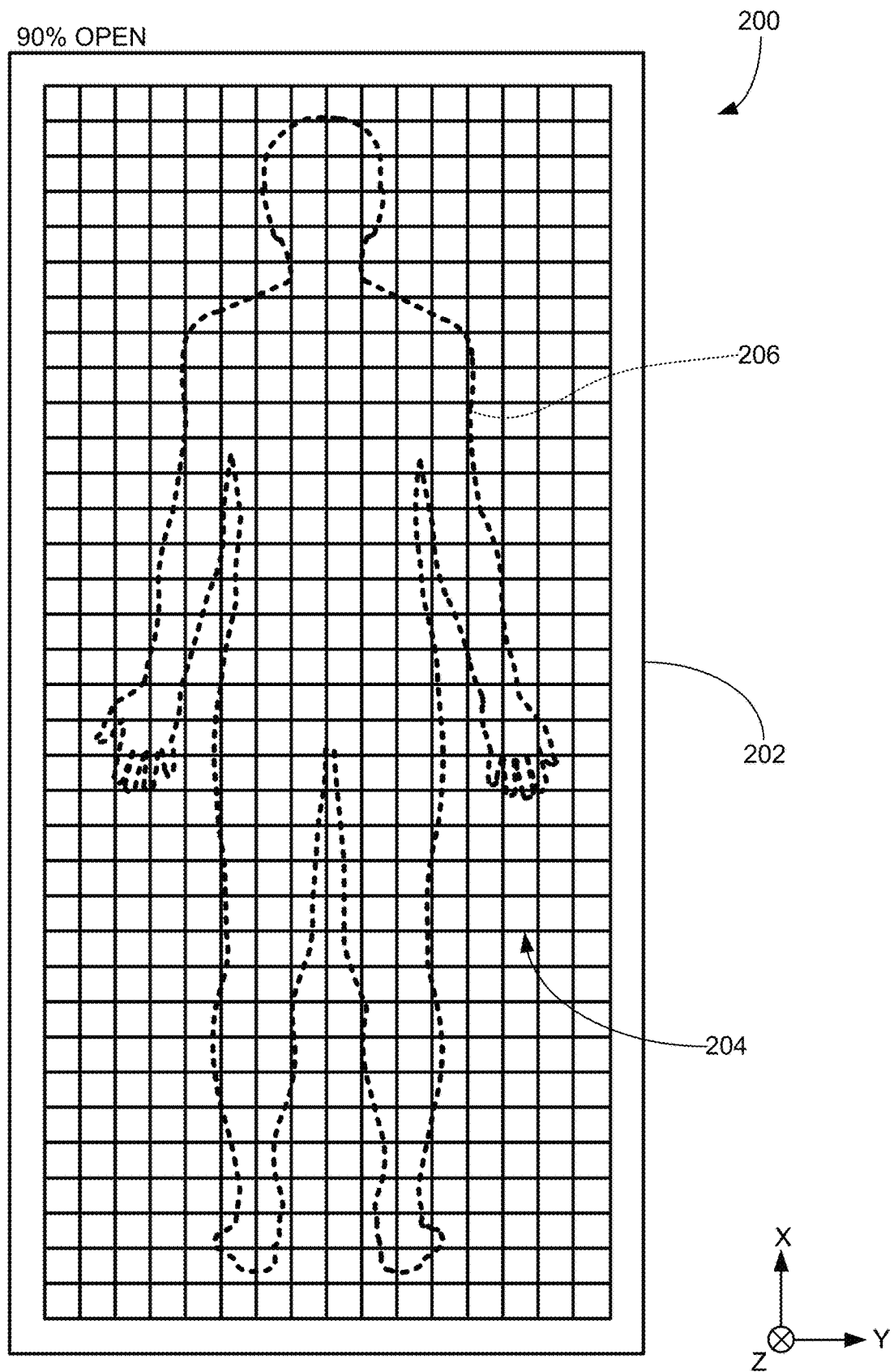
FIG. 7 is a schematic representation of another PBM light therapy bed of the system from FIG. 2 in some embodiments from a vantage point below the bed.

FIG. 7 is another schematic representation of a mesh structure 200 that can be incorporated into the various systems described herein. For reference, the view in FIG. 7 is upwards from below the structure (e.g., from the floor or base surface). The mesh structure 200 is shown to include a rectilinear framework 202 and a mesh 204 formed of variously arrayed strands. In this example, the mesh pattern takes the form of a rectilinear grid pattern with an open area ratio of about 90%.

A patient 206 is shown in dotted line form to represent the placement of the patent onto the mesh during a light therapy application session. The mesh 204 is not shown to be deformed for simplicity of illustration, but in practice it will be understood that the patient 206 would normally sag into and be conformably supported by the mesh 204. It can be seen from FIG. 7 that the mesh structure 200 is well adapted to irradiate the back side of the patient 206 during the session.

Figure 8:
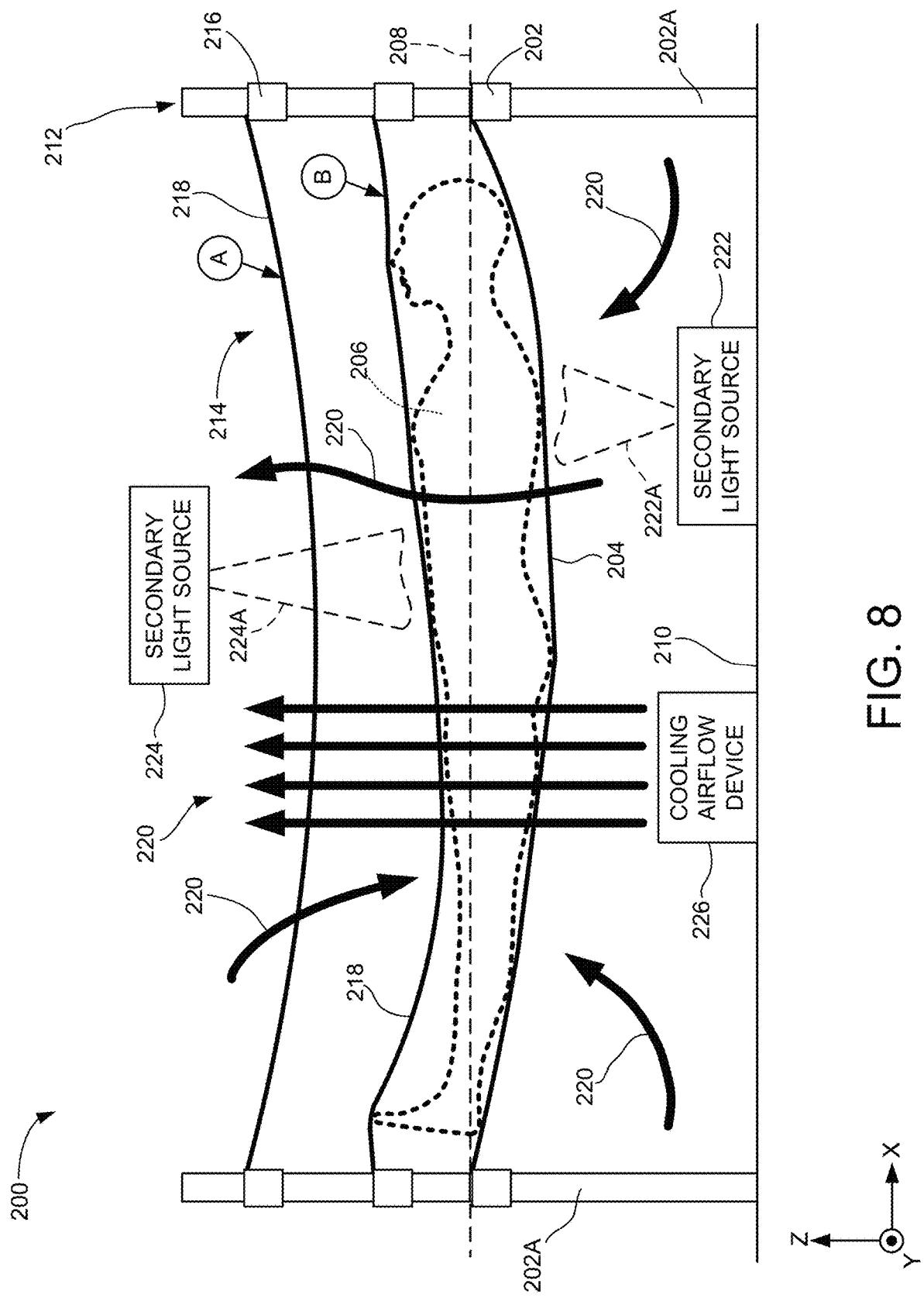
FIG. 8 is a schematic representation of the light therapy bed of the system in some embodiments from a side vantage point.

FIG. 8 is a side-view representation of the mesh structure 200 and patient 206 from FIG. 7. Aspects of the lower framework 202 from FIG. 7 have been omitted for clarity of illustration, but it will be understood that this element generally aligns along a planar mesh surface (broken line 208).

Support legs 202A support the structure 200 above a base (floor) surface 210. The conformal support provided to the patient 206 by the lower mesh 204 can be easily seen in FIG. 8; the actual amount of deflection of the mesh 204 will depend on a number of factors, including the tension applied to the mesh, the weight and size of the patient 206, etc.

An upper frame portion 212 extends upwardly to support an upper mesh structure 214 having a framework 216 and illuminating upper mesh 218. The upper mesh structure 214 is adjustable with respect to the upper frame portion 212 so that, once the patient 206 is comfortably placed onto the lower mesh 204, the upper mesh 218 can be lowered into a suitable position to irradiate the front side of the patient.

A first position (A) suspends the upper mesh 218 so as to be in close, non-contacting proximity to the patient 206. A second position (B) advances the upper mesh 218 so as to gently drape onto the patient 206. The mechanism may be adjustable so that any desired position for the upper mesh 218 can be provided as desired. The open nature of the respective meshes 204, 218 allow the free circulation and passage of air through the system, as generally denoted by arrows 220. This advantageously maintains the patient in a cool and comfortable state, reduces or eliminates perspiration or panic from the patient being confined in an enclosed space, and conforms the placement of the light sources for optimal spacing and effectiveness.

An optional lower secondary light source 222 is provided below the lower mesh 204, and an optional upper secondary light source 224 is supported above the upper mesh 218. The lower source 222 emits a secondary light beam 222A that passes through the apertures in the lower mesh 204 (see FIG. 7) to irradiate the underside of the patient 206, and the upper source 224 similarly emits a secondary light beam 224A that passes through the apertures in the upper mesh 218 to irradiate the front side of the patient.

The respective sources 222, 224 can be supported by the frame as required. In some cases, the lower source 222 can be supported directly on the underlying floor surface 210. Because of the open area provided by the respective meshes 204, 218, it is possible to position, adjust and direct any number of respective lower and/or upper light sources such as 222, 224 to irradiate the patient with secondary light or other electromagnetic radiation emissions during the concurrent application of primary light from the respective meshes (see e.g., beam 146A in FIG. 4A). The open area provided by the respective meshes 204, 218 further allows cooling air devices 226, such as fans, to direct forced airflow against and past the patient 206.

Bolster pads (not shown) can further be supplied to enhance the comfort of the patient 206. By way of illustration and not by limitation, a cylindrically shaped bolster could be supplied to bear up under the knee region of the patient to reduce hyperextension of the legs, a small neck support pillow could be used to support the neck of the patient, and so on. The bolsters can be formed of translucent or transparent material, such as with a clear outer cover formed of silicone, plastic, etc. and an internal, encapsulated soft and conformable filler material (a clear gel, water, clear plastic beads, etc.).

While the frameworks described herein have been generally rectangular in shape, this is merely illustrative and not limiting. Rather, any suitable shape, support or outline can be provided for the mesh. Similarly, it is not necessarily required that the entirety of the periphery of the mesh remain coplanar; further embodiments incorporate adjustability or contoured frameworks to meet the needs of a given application.

Figure 9A:
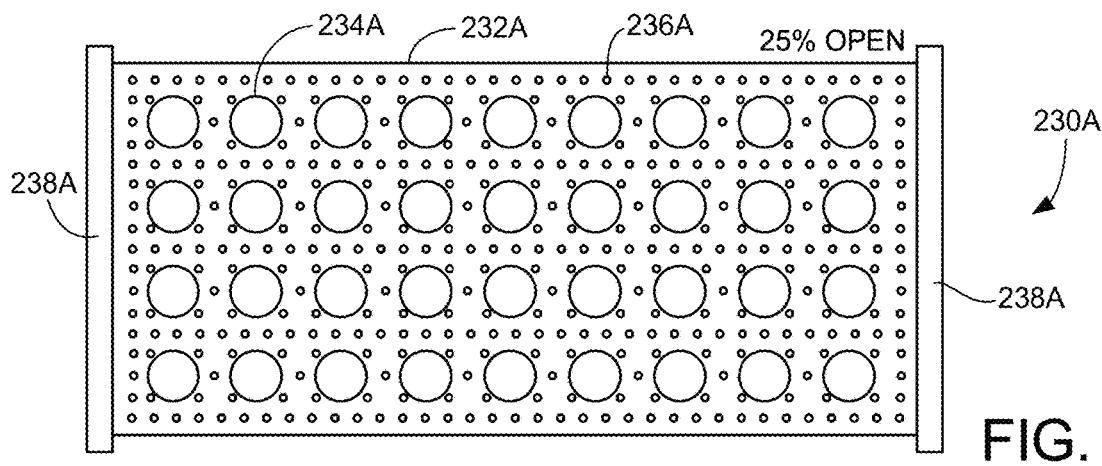
FIGS. 9A, 9B and 9C show further embodiments of another PBM light therapy bed in accordance with further embodiments.
Figure 9B:
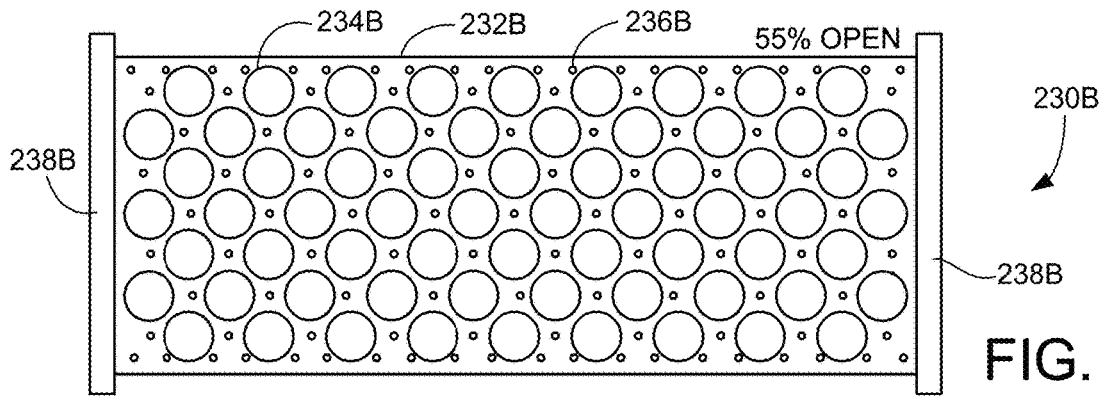
Figure 9C:
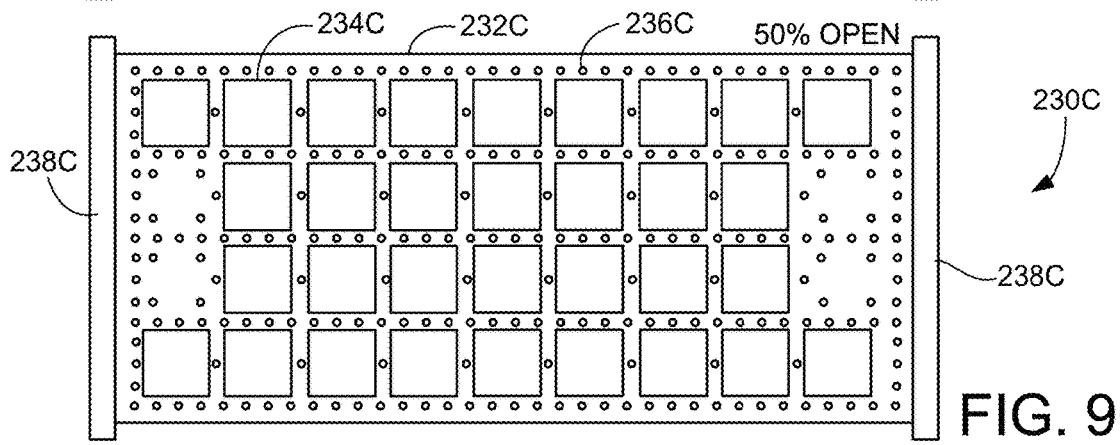

FIGS. 9A through 9C show additional configurations for PBM light therapy bed systems in accordance with further embodiments. FIG. 9A shows a first bed 230A having a mesh structure 232A that may include a soft complaint woven material such as canvas or other fabric. Extending through the mesh structure 232A are an array of spaced-apart, circular mesh apertures 234A. LEDs 236A are arranged in a pattern about the apertures to irradiate the patient as before.

A support frame 238A is formed of opposing support rails that support the longitudinally disposed ends of the mesh structure 232A, as is sometimes used with existing hammock-type devices. It will be noted that the laterally extending sides of the mesh structure 232A are not supported with similar support rails, although such can be provided as discussed above. In this case, the light therapy bed 230A has an open mesh area of about 25%.

FIG. 9B provides a second light therapy bed 230B with a configuration similar to that of FIG. 9A including fabric mesh structure 232B, mesh apertures 234B, LEDs 236B and support frame 238B. The arrangement of FIG. 9B has an open mesh area of about 55%.

FIG. 9C shows a third light therapy bed 230C with fabric mesh structure 232C, rectangular mesh apertures 234C, LEDs 236C and support frame 238C. The mesh pattern includes solid areas at each end to accommodate the respective head and feet of the patient. The bed 230C has an open mesh area of about 50%. It will be appreciated that each of the embodiments of FIGS. 9A-9C can be modified to provide other open mesh areas including configurations with open mesh areas of from about 20% up to about 90% as before.

Figure 10:
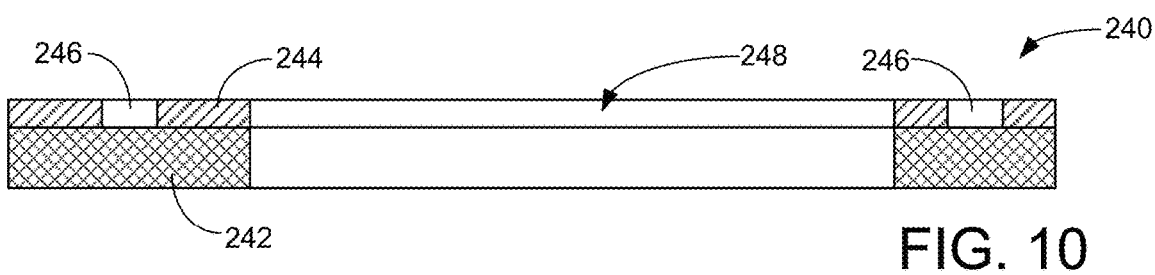
FIG. 10 is a cross-sectional representation of the embodiments of FIGS. 9A-9C.

FIG. 10 provides a cross-sectional view of a portion of another mesh bed 240 to illustrate an exemplary construction for each of the beds 230A-230C. The bed 240 has an underlying fabric reinforcement layer 242 that substantially extends across the entire areal extent of the bed. A light support layer 244 extends across a top surface to substantially cover the reinforcement layer 242 and includes embedded LEDs 246 arranged as before. Mesh apertures 248 extend through the respective layers 242, 244 in spaced apart fashion as required. It will be appreciated that those sections of the reinforcement layer 242 that extend across the bed 240 between the mesh apertures 248 can be characterized as non-illuminating strands, and those sections of the light support layer 244 extending across the bed 240 between the mesh apertures 248 can be characterized as illuminating strands.

Figure 11:
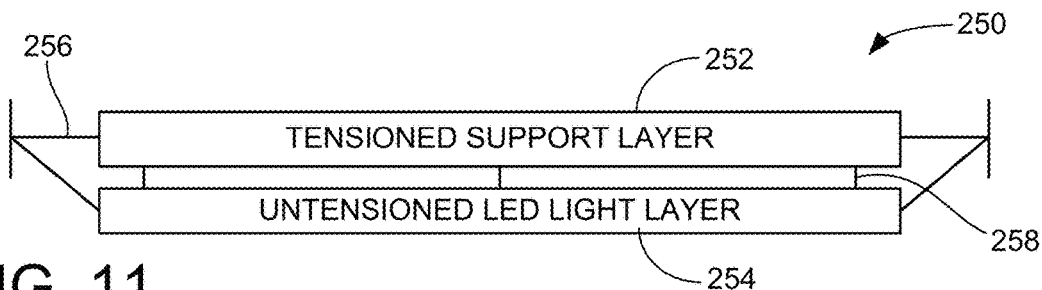
FIG. 11 is a functional block representation of a therapy system that incorporates another PBM light therapy bed in conjunction with a hyperbaric chamber in accordance with further embodiments.

FIG. 11 depicts another light therapy bed 250 constructed and operated in accordance with further embodiments. The bed 250 includes an upper tensioned support layer 252 and a lower untensioned LED light layer 254. Couplings 256 are used to connect the outer peripheral extents of each of the respective layers 252, 254 to a framework (not separately shown). As desired, additional couplings 258 can be used to interconnect the untensioned light layer 254 to the tensioned support layer 252 at selected locations as required.

The bed 250 is configured such that the tensioned support layer 252 contactingly supports and bears the weight of the patient. The underlying light layer 254 remains unloaded. The overlying support layer 252 can take a mesh configuration such as variously described above, and the open mesh area provided by the overlying support layer 252 allows the light emitted by the underlying light layer 254 to pass through the layer 252 and irradiate the underside of the patient.

Figure 12:
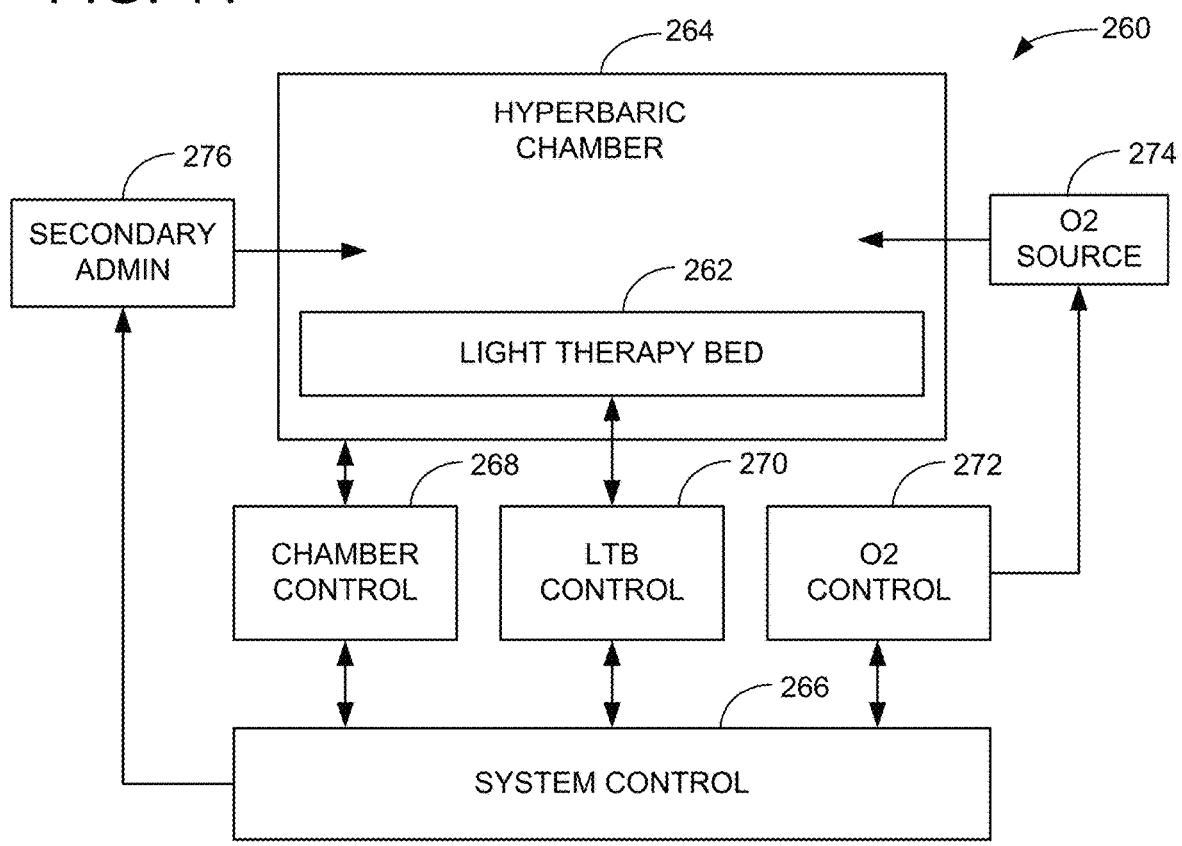
FIG. 12 is a schematic depiction of another PMB light therapy bed configuration in accordance with further embodiments.

FIG. 12 is a functional block representation of a multiple therapy administration system 260 constructed and operated in accordance with further embodiments to administer multiple therapies to a patient. In this case, light therapy is provided in combination with one or more additional therapies including hyperbaric oxygen (O2) therapy as well as one or more additional therapies as required.

The system 260 includes a light therapy bed 262 which is configured in accordance with one or more of the various alternative embodiments described previously to support a patient (not shown) and administer PMB light therapy. The light therapy session is carried out inside a hyperbaric chamber 264. In some embodiments, the bed 262 is configured such that the patient and the bed can be moved into and out of the chamber 264 as required.

As will be recognized by those skilled in the art, a hyperbaric chamber such as 264 is a relatively large pressurizable vessel sized to accommodate a patient in a prone or sitting position. The vessel includes a pressure door and reinforced sidewalls (not separately shown) to allow the patient to be safely enclosed and sealed within the chamber. An increase in ambient pressure is applied within the pressure vessel, such as some percentage above normal atmospheric pressure. Oxygen supply lines are routed to the patient via a mask or similar to allow the patient to breath pure O2 while the increased surrounding pressure facilitates absorption of the O2 by the patient's tissues.

In the system 260 of FIG. 12, the patient undergoing hyperbaric O2 treatment within the chamber 264 is further supplied with light therapy by the bed 262. As required, a secondary protocol such as blood ozonation, etc. is also applied.

To this end, the system 260 further includes a system control circuit 266 that provides top level control and monitoring of the applied therapies. The system control circuit 266 respectively communicates with a chamber control circuit 268 to facilitate operation of the chamber 264, a light therapy bed (LTB) control circuit 270 to control operation of the bed 262, an O2 control circuit 272 to modulate an O2 source 274 and, as required direct control of a secondary administration control unit 276 for the administration of a secondary protocol.

It has been found that applying light therapy during hyperbaric O2 therapy can advantageously provide a number of therapeutic benefits for a patient. The light weight, portable nature of the light therapy beds as variously embodied herein make such particularly suitable for use within a chamber such as 264.

Figure 13:
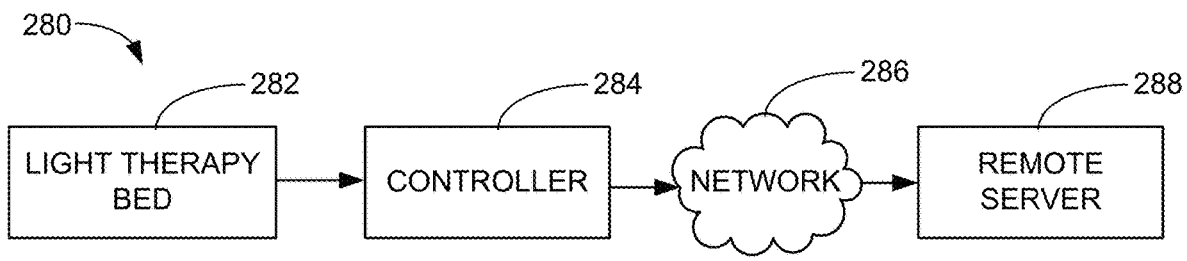
FIG. 13 is a functional block representation of a communication system that incorporates another PBM light therapy bed in accordance with further embodiments.

FIG. 13 provides another light therapy treatment system 280 in accordance with further embodiments. The system includes a light therapy bed 282 which may be configured as described herein (e.g., upper and lower mesh structures, framework, various support elements, etc. A controller 284 operates as described above to monitor and control the therapy process.

During, prior to, or after the session, the controller 284 may communicate, via a network 286 (including but not limited to the Internet), with a remote server 288. This provides significant flexibility in patient treatment, including but not limited to remote activation and operation, cloud storage of patient records and other information, and so on. The system can thus be used to provide enhanced treatment options, including based on non-personally identifiable information across a class of patients.

Figure 14:
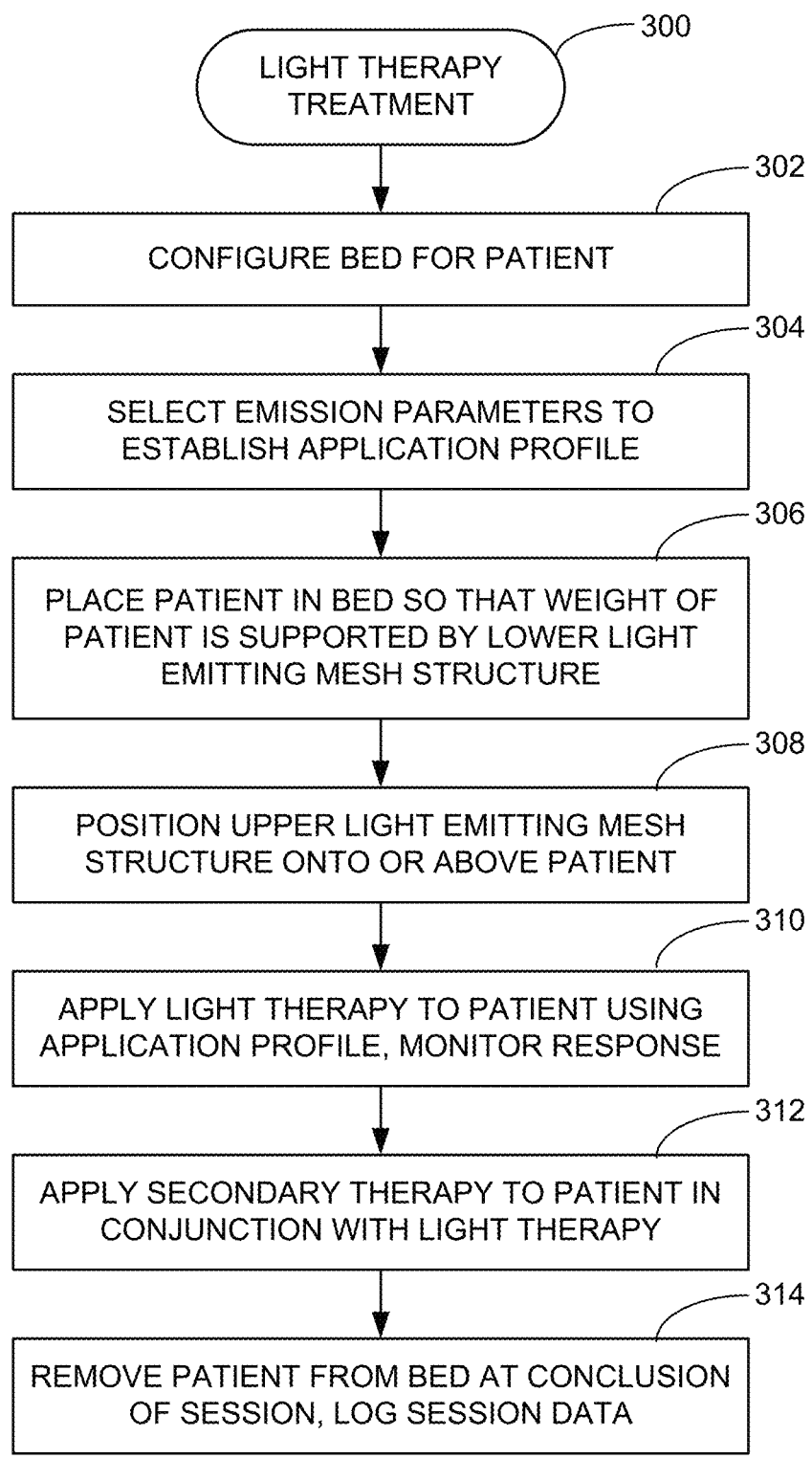
FIG. 14 is a flow chart for a light therapy treatment routine illustrative of exemplary steps that may be carried out in accordance with various embodiments to administer light therapy to a patient.

FIG. 14 provides a flow chart for a light therapy treatment routine 300, generally illustrative of steps that may be carried out in accordance with the foregoing discussion. Other steps may be used.

The routine 300 commences at step 302 with the configuration of a light therapy bed system, such as described herein, for a particular patient treatment session. This can include mechanical configurations of the system including adjustments to the height of a lower light emitting mesh structure, the installation of appropriate LED modules at different locations along the support structure, etc.

Once configured, an appropriate set of emission parameters are selected for the light therapy session at step 304. This can include the selection of various wavelengths, pulse lengths, waveforms, timing intervals, intensities, light distances, and other factors relating to the session. This can be specified in an application profile. In some cases, the profile can be stored in memory and selected by the administrator. A set of profiles can be predetermined and selected as required, or individually tailored profiles can be generated for each session based on feedback and history trends relating to the patient.

At step 306, the patient is placed onto the bed by maneuvering onto the lower mesh structure. The mesh structure will operate as described herein to conformally support some or all of the weight of the patient. It will be appreciated that the patient may be partially disrobed in order to expose a maximum amount of skin to the system for irradiation, as is customary with existing systems. Similarly, the patient may wear protective eyewear, etc. as part of the treatment process.

As desired, an upper light emitting mesh structure is next brought into close proximity of the patient at step 308. As described previously in FIG. 8, the upper structure can be brought into contact with, or suspended above, the patient, in order to irradiate the front side of the patient. Some embodiments provide adjustability in the frame to contour the upper mesh so as to curvilinearly extend about the patient at a desired distance to achieve the desired intensity. Because of the open nature of the mesh structures, the patient can comfortably nest between the layers with little or no discomfort. The aforementioned sensors (see e.g., FIGS. 1, 3) can include light intensity feedback sensors incorporated into or on the mesh structure that measure the received light and allow adaptive adjustments to appropriate levels by the patient.

At step 310, the light therapy session commences by irradiating the patient using the upper and lower mesh structures. The irradiation takes place in accordance with the selected application profile. The system can be closed-loop and adaptive, so that changes may be made to the applied light based on sensor or patient monitor readings.

As required, a secondary therapy protocol may be applied to the patient during the light therapy treatment, as shown by step 312. This second therapy protocol can include any of the above described therapies including but not limited to hyperbaric O2 treatment, medication, blood ozonation, etc., as well as any other suitable therapy or therapies as desired.

At step 314, at the conclusion of the treatment session, the patient is removed from the structure, such as by getting out of the bed, getting dressed, etc. System information collected during the session is accumulated and logged for further analysis, including in use for selecting a subsequent treatment profile.

A number of alternative and/or additional steps can be incorporated into the routine. Blood sampling of the patient can be carried out both before and after the light therapy session. Various treatments can be provided during the light therapy session such as administered via an IV, including the use of methylthionine chloride ("methylene blue") or other substances that can promote mitochondrial stimulation or other beneficial effects. Oxygen, blood ozonation, TMS, acoustic stimulation, and/or other treatments can be readily accommodated through the open frame nature of the system. As noted previously, because of the open mesh nature of the support, secondary emission systems can be placed above or below the respective mesh structures for further application to the patient (e.g., electromagnetic radiation from a secondary light source, etc.).

While various embodiments have contemplated the use of a light therapy bed as a particularly suitable configuration for the system, other arrangements can be used such as a chair, bench, recliner, etc. The various mechanisms that provide tensioning and adjustments can be configured in a number of ways including ratchets, spring bars, latches, hook and loop fasteners, etc. Monitored session data can be captured for heuristic analysis, including using confidential machine learning systems.

Substantially any range of therapeutic wavelengths of light can be used, including but not limited to wavelengths within the range of from about 500 nm up to about 1500 nm. Other wavelengths can be used including wavelengths above or below this range. Waveforms can be tailored to any shape including sinusoidal, square, sawtooth, stepped, sloped, etc. Time varying PWM and time-between pulse profiles can be used. Secondary light sources can further be used to irradiate the patient with additional light energy that passes through one or more of the meshes.

It is to be understood that even though numerous characteristics and advantages of various embodiments of the present disclosure have been set forth in the foregoing description, together with details of the structure and function of various embodiments of the disclosure, this detailed description is illustrative only, and changes may be made in detail, especially in matters of structure and arrangements of parts within the principles of the present disclosure to the full extent indicated by the broad general meaning of the terms in which the appended claims are expressed.

What is claimed is:

1. An apparatus comprising:
a rigid support frame;
a photobiomodulation (PBM) mesh structure supported by the frame to form a patient support surface adapted to contactingly support a patient above an underlying base surface, the mesh structure comprising a plurality of spaced apart illuminating strands interconnected with a plurality of spaced apart non-illuminating strands, each of the illuminating strands comprising a series of light sources enclosed within an outer sleeve comprising an enclosed tube of transparent flexible material through which electromagnetic radiation in the form of emitted light passes to impinge upon a dermal region of the human patient, each of the non-illuminating strands comprising a substantially non-elastic reinforcement member, the mesh structure further providing an array of mesh apertures extending between adjacent pairs of the illuminating strands to provide an open mesh arrangement;

a tensioner configured to adjustably apply tension to the PBM mesh structure during contacting support of the patient, the tensioner applying a higher, first tension to each of the non-illuminating strands while concurrently applying a lower, second tension to each of the illuminating strands so that the non-illuminating strands bear a greater amount of a weight of the patient and the illuminating strands bear a lesser amount of the weight of the patient; and a control circuit configured to supply electrical power to the mesh structure to supply light therapy to the human patient via the illuminating strands at a selected wavelength.

2. The apparatus of claim 1, wherein the PBM mesh structure has an open mesh area formed by the array of mesh apertures of at least 50% of an overall areal extent of the PBM mesh structure, and wherein each mesh aperture is bounded by two immediately adjacent illuminating strands and two immediately adjacent non-illuminating strands.

3. The apparatus of claim 2, wherein the open mesh area is at least 75% of the overall areal extent of the PBM mesh structure.

4. The apparatus of claim 1, wherein the non-illuminating strands contactingly support the patient to bear substantially a full weight of the patient, wherein the illuminating strands are disposed wholly below the non-illuminating strands and do not contactingly support the patient, and wherein the electromagnetic radiation emitted by the light sources passes between adjacent pairs of the non-illuminating strands to impinge upon the dermal region of the patient.

5. The apparatus of claim 1, wherein the tensioner comprises at least a selected one of a ratchet, a spring bar, a latch, or a hook and loop fastener.

6. The apparatus of claim 1, wherein the PBM mesh structure comprises a plurality of interconnectable modules each comprising an associated set of the light sources that provide the emitted electromagnetic radiation in a different range of wavelengths.

7. The apparatus of claim 1, wherein the light sources emit the electromagnetic radiation within a range of from nominally 500 nanometers, nm to nominally 1500 nm.

8. The apparatus of claim 1, wherein the PBM mesh structure is characterized as a lower PBM mesh structure configured to irradiate a backside of the patient, and wherein the apparatus further comprises an upper PBM mesh structure supported by the frame at a position above the lower PBM mesh structure to concurrently direct electromagnetic radiation upon a frontside of the patient.

9. The apparatus of claim 8, wherein the rigid support frame comprises an adjustment mechanism configured to raise and lower the upper PBM mesh structure relative to the lower PBM mesh structure.

10. The apparatus of claim 9, wherein the adjustment mechanism is configured to lower the upper PBM mesh structure in contacting, draping arrangement onto the patient so that both the upper and lower PBM mesh structures concurrently emit the respective electromagnetic radiation onto the patient during contact therewith.

11. The apparatus of claim 9, wherein the adjustment mechanism is configured to contactingly drape the upper PBM mesh structure onto the frontside of the patient.

12. The apparatus of claim 1, further comprising a cooling device disposed below the PBM mesh structure configured to direct a flow of forced cooling air through the mesh apertures and adjacent the patient to cool the patient during the application of the electromagnetic radiation.

13. The apparatus of claim 1, wherein each of the reinforcement members comprises a fabric material.

14. The apparatus of claim 1, wherein the light sources comprise light emitting diodes (LEDs) configured to emit the light at the selected wavelength.

15. The apparatus of claim 1, wherein the control circuit activates the light sources in response to an activation profile that provides modulated pulses of the emitted light at selected pulse frequencies and durations.

16. The apparatus of claim 15, wherein the activation profile provides a plurality of different wavelengths of light using a predetermined light modulation pattern at selected power levels for a predetermined distance from the patient.

17. A method for applying photobiomodulation (PBM) light therapy to a patient, comprising:

supporting the patient on a PBM mesh structure coupled to a rigid frame, the PBM mesh structure comprising a plurality of spaced apart illuminating strands interconnected with a plurality of spaced apart non-illuminating strands to form a conformable, open mesh support structure having an array of mesh apertures extending therethrough, the PBM mesh structure further comprising a tensioner coupled between the frame and the non-illuminating strands to apply a first tension to each of the non-illuminating strands while concurrently applying a lower, second tension to each of the illuminating strands so that the non-illuminating strands bear substantially all of an overall weight of the patient and the illuminating strands bear substantially none of the overall weight of the patient; and activating a series of light sources within the illuminating strands to generate electromagnetic radiation in the form of emitted light which impinges upon a dermal region of the human patient, the light sources activated by a control circuit configured to supply electrical power to the mesh structure to supply light therapy to the human patient via the illuminating strands at a selected wavelength.

18. The method of claim 17, wherein the PBM mesh structure has an open mesh area formed by the array of mesh apertures of from nominally 20% to nominally 90% of an overall areal extent of the PBM mesh structure.

19. The method of claim 17, wherein the PBM mesh structure has an open mesh area formed by the array of mesh apertures that is at least 50% of an overall areal extent of the PBM mesh structure.

20. The method of claim 17, wherein the PBM mesh structure is a lower PBM mesh structure, and the method further comprises:

providing an upper PBM mesh structure above the lower PBM mesh structure;

lowering the upper PBM mesh structure to a position in close proximity to the patient; and activating a second series of light sources within the upper PBM mesh structure to irradiate the patient with emitted light therefrom.

21. The method of claim 20, further comprising using an adjustment mechanism affixed to the upper PBM mesh structure to contactingly drape the upper PBM mesh structure onto a frontside of the patient.

22. The method of claim 17, further comprising steps of administering hyperbaric O2 therapy to the patient using a hyperbaric chamber during the activating step.

23. The method of claim 17, further comprising directing a cooling flow of air upwards through the mesh apertures to cool the patient during the activating step.

24. The method of claim 17, further comprising directing a second set of electromagnetic radiation onto the dermal region of the patient from a secondary light source disposed below the PBM mesh structure, the second set of electromagnetic radiation passing through the mesh apertures in the PBM mesh structure to the patient.

25. The method of claim 17, further comprising adjusting an intensity of the emitted light which impinges upon the dermal region of the human patient responsive to an application profile that adjusts at least a selected one of wavelength, power, pulse duration and intensity.

* * * * *